United States Patent [19]

Martin

[11] Patent Number: 4,846,685
[45] Date of Patent: Jul. 11, 1989

[54] PERFORATED DENTAL POST SYSTEM

[76] Inventor: Howard Martin, 909 Pershing Dr., Silver Spring, Md. 20910

[21] Appl. No.: 178,262

[22] Filed: Apr. 6, 1988

[51] Int. Cl.⁴ ............................................. A61C 5/08
[52] U.S. Cl. .................................................... 433/221
[58] Field of Search ............................... 433/220, 221

[56] References Cited

U.S. PATENT DOCUMENTS

| | | | |
|---|---|---|---|
| 430,522 | 6/1890 | Genese | 433/221 |
| 4,759,714 | 6/1988 | Szegvary | 433/221 |

Primary Examiner—Robert Peshock
Attorney, Agent, or Firm—Walter G. Finch

[57] ABSTRACT

A perforated dental post system is provided for anchoring a crown to the root of a tooth. This post consists of a shank with a spiral thread running lengthwise thereof. Serrations are provided on the shank. Flanges are provided at the upper end of the post. A central bore runs lengthwise of the post, and spaced transverse or perpendicular cross bores are provided in the post. When the bores are filled with cement and the outer wall of the post is coated with cement, the post can be anchored to the tooth root and to the crown. In a second embodiment of the dental post, a plurality of longitudinally extending grooves are provided in the surface of the post together with a plurality of shallow longitudinally and radially extending bores. When the various bores and grooves are filled with cement, they can be used to anchor the post in a tooth.

15 Claims, 1 Drawing Sheet

PERFORATED DENTAL POST SYSTEM

BACKGROUND AND SUMMARY OF THE INVENTION

This invention relates to dental devices for securing a crown to the tooth root in position.

With the development in dentistry of improved restorative procedures and predictable root canal therapy, the advent of intracanal anchors known as posts has become an integral factor in restorative dentistry.

Some of the prior art relating to dental posts is set forth in the Deutsch et al patents listed below:

| PATENT REFERENCES | | | |
|---|---|---|---|
| U.S. Pat. No. | Date | Inventor | Title |
| 4,480,997 | 11/06/84 | Deutsch et al | Dental Post and Wrench Therefor & Method of Restoring Bulk to a Tooth Root Therewith |
| 4,490,116 | 12/25/84 | Deutsch et al | Dental Post and Wrench Therefor & Method of Restoring Bulk to a Tooth Root Therewith |
| Re. 31,948 | 07/16/85 | Deutsch et al | Dental Post & Wrench Therefore & Method of Restoring Bulk to a Tooth Root Therewith |

Originally cast dowels into prepared root canals were advocated as a post for holding crowns to the root after root canal therapy. It was shown that a properly adapted post serves to evenly transmit the internal stresses through the post to the root structure without undue stress at any one point.

Post and cores are to provide necessary strength and even more importantly retention for the crowns. Adequate post retention is the key factor. Areas of question have been in the taper (parallel vs. tapered), threaded-serrated versus smooth sided, apical configuration, angulations, all points leading to stress fractures and loss of retention.

It has been shown that the length of the post is statistically significant, with the longer the post the more support. The remaining dentin thickness between the apical level of the post and surface of the tooth is significant in relation to root fracture. It has also been shown that surface roughness improved axial retention.

Post design has a very definite effect on retentive capacity. Serrated cemented posts showed an intermediate retentive ability while threaded posts were superior. Post diameter did not show any significant evidence on retentive capacity larger ones were detrimental due to weakening of root structure.

The more acceptable approach is to prepare as narrow a post channel as compatible with root strength in order to preserve root material and reduce the possibility of perforation.

Smaller diameter posts maintain less contact with the dentin and avoids weakening the root. This embedment depth is also inhibited by the amount of root canal filling which must remain within the root canal in order to prevent apical leakage and failure of the root canal filling material.

The amount of root canal filling that must be left within the canal is at least 4–5 mm from the apex of the canal. Therefore, embedment cannot be any closer than 5 mm from the apex of the root. Anatomical curvatures also reduce the embedment depth as a post is not flexible and can only be placed in a straight channel thereby also reducing embedment depth. Depths of embedment did not show significant improvement between a 5 mm and an 8 mm depth.

Parallel sided, serrated vented posts fail by dislodgement with cement adhering to the post. Smooth posts fail completely at the cement post interface. The main factors influencing preformed post retention are design and depth of embedment. Type of cement and diameter have little or no effect.

The retention of cemented posts relies on their adaptation to the channel wall, the less the mismatch between the post and channel, the greater the retention. Cemented posts are more reliant upon a uniformly thin film of cement but the canal morphology and ability to match a drilled channel and post is extremely difficult.

The most retentive types based upon previous research is the threaded parallel sided post screwed slightly into dentin canal wall, so as to engage the channel wall, with cement.

The proper criteria than that evolves in developing a proper post is based upon a proper understanding of general biologic, anatomic, and engineering principles. Most investigators attribute post failure to the problem of retention.

Further studies of an engineering type nature show that tensile and torsional forces must also be considered. Based upon tension and torsion studies, the surface configuration of the post is a more important variable then length. The values needed for loss of retention under torque were much smaller than under tension.

This indicates, for increased resistance to dislodgement, the concentric type post should have an anti-rotational feature (suggested has been irregular surface, pin or groove). Torsional failure starts imperceptibly as a minor movement as compared to tensile withdrawal.

Tapered posts create a wedging effect with stress formation at the shoulder angle while smooth sides parallel posts generate the maximum apical stress, thus requiring a properly designed stress free apex.

Another problem that must be considered is a cementation groove to vent the hydrostatic pressure developed during insertion and cementation in threaded posts, the elasticity of the dentin and cement is a key factor. However, the threads or serrations are really a series of sharp line angles that can lead to minute fractures under stress during insertion or masticatory forces.

A second problem is the proper venting of the hydrostatic pressure developed during the cementation process which relies on an oblique movement along the threads. What is required is minimal insertion pressure to avoid root fracturing. Passive insertion may not lock the post into the channel and therefore may rely totally on a cement lock on the post surface which is at best highly questionable.

Though smooth posts develop the least stress, they also provide the least retention. The retention is based almost entirely upon the cement. Serrated threaded post increase retention but also increase stress. The practical clinical characteristics which would be best are for a long, narrow, parallel sided, threaded vented post.

Parallel sided vented posts when dislodged had most of the cement adherent to the post. This indicates that there is required a dentin wall attachment. Smooth tapered posts leave cement in the channel and fail at the post cement interface. This indicates that some type of cement bonding within the post itself is necessary.

Endodontically treated teeth restored with smaller diameter posts provide increased resistance to fracture. In order to facilitate this, the short post will need a definite anchoring system. Increased post diameter increases stress showing that strength of the root is directly related to bulk of remaining dentin.

Many of the angular and vertical fractures can be attributed to hydraulic pressures occurring during cementation. This shows that a proper venting system is required. A positive function of cement is that it acts as a stress buffer and maximum post adaptation to the channel may not be desirable. This requires a post design that enables cement to attach, stress break, and maintain retention all at the same time.

Coating cement onto the post gives little hydrostatic pressure but results in an incomplete bond whatever the shape of the post. With the cement placed into the post hole there is always pressure. Vented posts are necessary to obtain proper cement coverage and good retention without excessive intra-radicular hydrostatic pressure.

Spiral channels are one way to vent cement, albeit a poor and unpredictable method. Failure of the cement may also be due to the surface condition of the dentin wall. A smear layer may prevent good cement-dentin contact and reduce retention. Cleaning agents may improve dentin cement contact. A method to improve cement-post contact is required.

It is the purpose of this invention to overcome these deficiencies by providing a post that is parallel sided to maintain the retention and create the least stress.

The post will have serrated threads approximately each millimeter in order to create greater surface area and contact along the canal wall. The post will have provided between the serrated threads a bore hole perpendicular to the longitudinal axis of the post.

The end of apical portion of the post will be rounded to avoid severe wedging forces with the purpose of the bore hole being to enable the cement to make contact within the post locking the cement within and without along the wall of the post and also into the dentinal tubules, which have been previously cleaned with an acid solution removing the smear layer. What is developed is a + + of cement bonding the post into the canal and also acting as an anti-rotational device. Venting is through the oblique serrations and the hole locking mechanism.

An important modification within this concept is to have the post with the above serrations and bore holes along with the post having a vertical bore hole coming out through the coronal portion initiating from the apical end to act as a further vent and also as a further locking mechanism. This will create a cross lock plus another vertical lock of cement developing the + + +double HH locking design. This gives increased retention and anti-rotation.

It is an object of this invention to provide a parallel sides dental post having oblique serration threads for use in anchoring a tooth of a person.

Another object of this invention is to provide a dental post which has perforation bore holes or apertures arranged perpendicular to the longitudinal axis of the post and positioned between the serration threads for anchoring of teeth of a person.

Still another object of this invention is to provide a dental post which has a central bore hole from the apex to the coronal end of the post.

And still another object of this invention is to provide a dental post having serration threads and a central bore hole from the apex exiting through the coronal end.

And even another and further object of this invention is to provide a dental post formed of stainless steel, titanium or various type metals and alloys that are non-corroding.

BRIEF DESCRIPTION OF THE DRAWINGS

These and other objects and attendant advantages of this invention will become more obvious from the following drawings and description in which.

DESCRIPTION OF THE PREFERRED EMBODIMENTS

Figures 1, 2, 3, 4, 5:
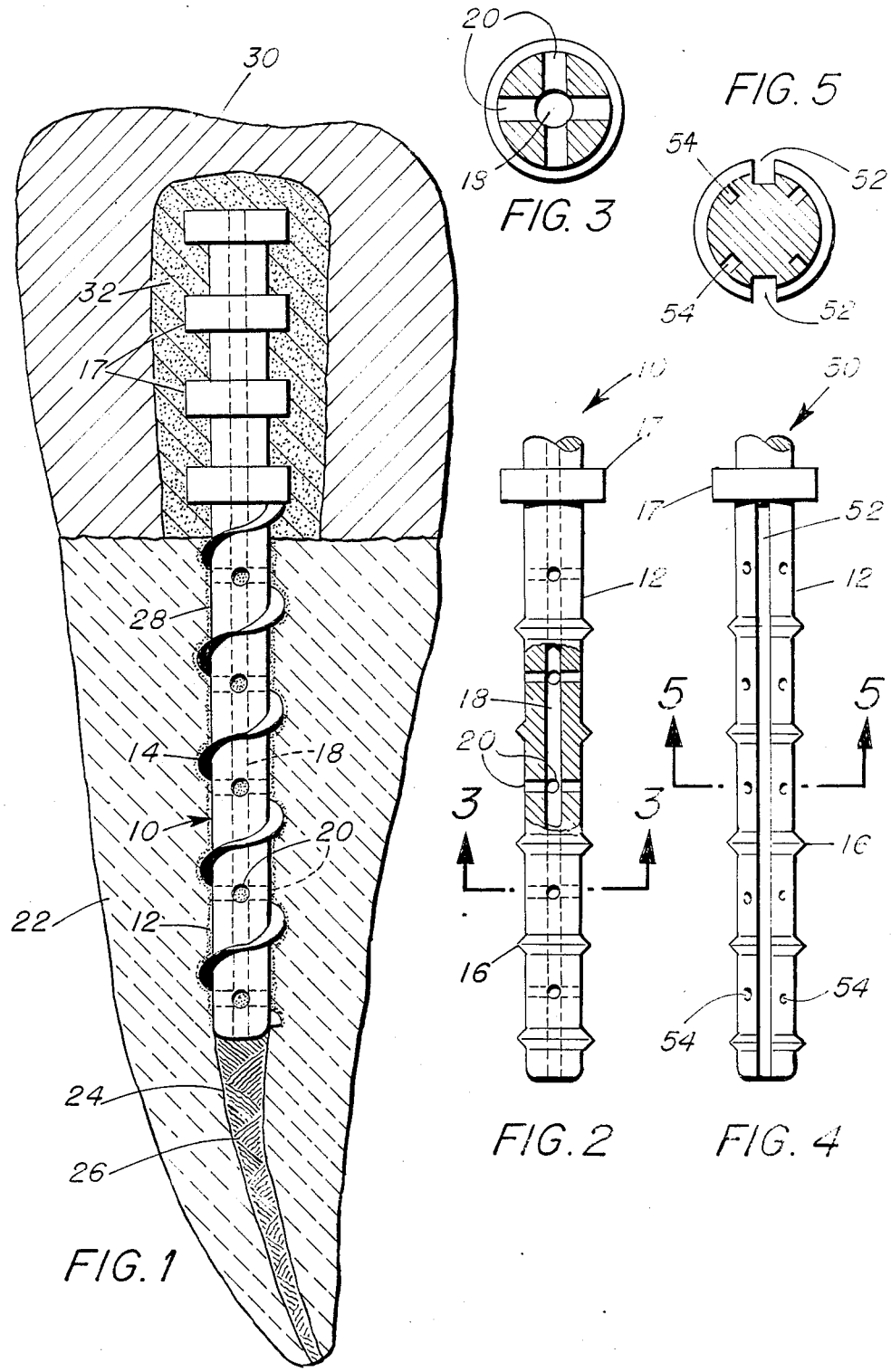
FIG. 1 is an enlarged cross section taken through a tooth of a person, with the preferred first embodiment of the dental post being of a screw-in type known as active and shown in elevation.
FIG. 2 is an enlarged view, partially in cross section, of a serrated push-in dental post, corresponding to the first embodiment of the invention of FIG. 1.
FIG. 3 is a cross section taken along line 3—3 of FIG. 2.
FIG. 4 is a second embodiment of a dental post.
FIG. 5 is a cross section taken along line 5—5 of FIG. 4.

Referring now to FIGS. 1 to 3 of the drawings, there is shown generally the preferred embodiment of a dental post 10 having a cylindrical shank 12 with a spiral thread 14 located on the peripheral surface and extending in a longitudinal direction lengthwise thereof. The pitch of the spiral thread 14 is exaggerated for purposes of clarity.

Serrations 16, shown best in FIG. 2, are provided on the shank 12. As shown at the upper end of the dental post 10, flanges 17 are also provided.

A central bore 18 is provided in post 10, and it runs lengthwise of the post 10, as shown in FIGS. 1 and 2. Spaced transverse or perpendicular cross bores 20 are provided and they are through bores in the post 10.

As shown in FIG. 1, the tooth root 22 has a canal 24 and a gutta percha 26.

After the tooth root 22 is prepared to receive the post 10, suitable cement 28 is placed along the inner surface of the post hole and in the central bore of the post 10 after the post 10 is placed in position utilizing the spiral threads 14, with the cross bores 20 likewise being filled with cement as shown best in FIGS. 1 to 3.

The crown 30 is then filled with crown cement 32 and then anchored to the flanges 17 of the post 10 to anchor the crown to the tooth root 22.

Referring now to FIGS. 4 and 5, there is shown a modified central post 50 that differs from the dental post 10 of FIGS. 1 and 2 in the provision of the four longitudinally positioned grooves 52 which run lengthwise of the post 50 and are spaced approximately 90 around the surface of the post 50. Shallow spaced radial bores 54 are positioned radially and longitudinally of the post 50. These bores 54 and grooves 52 are filled with cement 28 and 32 to anchor the crown 30 to the tooth root 22.

Accordingly, modifications and variations to which the invention is susceptible may be practiced without departing from the scope and intent of the appended claims.

What is claimed is:

1. A dental post for anchoring a crown to the root of a tooth, comprising, shank means having substantially parallel sides extending longitudinally thereof, at least one protuberance positioned on the peripheral surface of said shank means and extending in a longitudinal direction of said shank means substantially lengthwise thereof, said shank means also being provided with spaced apertures arranged perpendicularly to said shank means, said spaced apertures in said shank means being positioned about said protuberance for anchoring said crown to said root of said tooth.

2. A dental post for anchoring a crown to the root of a tooth as recited in claim 1, wherein said shank means is provided with a central bore therein extending substantially from the apex and to the coronal end of said shank means.

3. A dental post for anchoring a crown to the root of a tooth as recited in claim 1, wherein a plurality of protuberances are provided on said shank means and consist of serrated threads arranged obliquely to the longitudinal direction of said shank means and a central bore extending from the apex of said shank means and exiting through the coronal end of said shank means.

4. A dental post for anchoring a crown to the root of a tooth as recited in claim 1, and radially spaced longitudinally arranged bores positioned on the outer surface of said shank means and running lengthwise thereof.

5. A dental post for anchoring a crown to the root of a tooth as recited in claim 1, and a plurality of shallow radially extending spaced bores positioned on the peripheral surface of said shank means and also spaced longitudinally along said length of said shank means.

6. A dental post for anchoring a crown to the root of a tooth as recited in claim 1, wherein said protuberances are of spiral shape running lengthwise of said shank means.

7. A dental post for anchoring a crown to the root of a tooth as recited in claim 1, wherein a plurality of longitudinally extending spaced channels are provided in the peripheral surface of said shank means for receiving cementitious material.

8. A dental post for anchoring a crown to the root of a tooth as recited in claim 7, wherein said channels are equally spaced around the peripheral surface of said post.

9. A dental post for anchoring a crown to the root of a tooth as recited in claim 7, wherein said channels are unequally spaced around the peripheral surface of said post.

10. A dental post for anchoring a crown to the root of a tooth as recited in claim 1, and cementitious material positioned on said protuberances and said apertures for aiding in holding said shank means to said crown and root of said tooth.

11. A dental post for anchoring a crown to the root of a tooth as recited in claim 1, wherein said protuberance on said shank means consists of spaced serration means arranged substantially perpendicularly to the longitudinal direction of said shank means and positioned in the longitudinal direction thereof.

12. A dental post for anchoring a crown to the root of a tooth as recited in claim 1, wherein said protuberance is a spiral positioned on the peripheral surface of said shank means and runs substantially lengthwise thereof.

13. A dental post for anchoring a crown to a root of a tooth as recited in claim 12, wherein said spiral is continuous on the peripheral surface of said shank means.

14. A dental post for anchoring a crown to a root of a tooth as recited in claim 12, wherein said protuberance consists of a plurality of spaced serrations arranged along the peripheral surface of said shank means and in the longitudinal direction thereof.

15. A dental post for anchoring a crown to a root of a tooth as recited in claim 12, wherein said protuberance consists of spaced flange means arranged along the peripheral surface of said shank means and in the longitudinal direction thereof.

* * * * *